United States Patent [19]

Hathaway et al.

[11] 4,278,883
[45] Jul. 14, 1981

[54] SAMPLE MOUNT FOR X-RAY DIFFRACTION

[75] Inventors: John C. Hathaway, Falmouth; Lawrence J. Poppe, East Falmouth, both of Mass.

[73] Assignee: The United States of America as represented by the Secretary of the Interior, Washington, D.C.

[21] Appl. No.: 108,260

[22] Filed: Dec. 27, 1979

[51] Int. Cl.³ .............................................. G01N 23/20
[52] U.S. Cl. ............................. 250/277 CH; 250/272
[58] Field of Search ............... 250/272, 273, 277 CH, 250/491; 356/244

[56] References Cited
U.S. PATENT DOCUMENTS

| | | | |
|---|---|---|---|
| 3,340,397 | 9/1967 | Johnston | 250/277 CH |
| 3,536,912 | 10/1970 | Speck et al. | 250/277 CH |
| 3,852,594 | 12/1974 | Paolini | 250/277 CH |
| 4,037,109 | 7/1977 | Hosokawa et al. | 250/272 |
| 4,078,175 | 3/1978 | Fletcher et al. | 250/277 CH |
| 4,115,689 | 9/1978 | Won | 250/277 CH |

Primary Examiner—Davis L. Willis
Attorney, Agent, or Firm—Thomas Zack; Donald A. Gardiner

[57] ABSTRACT

A sample mount assembly for use with an X-ray diffractometer. The assembly includes a holder with an opening extending therethrough, an insert to fit into the holder through its opening, a substrate filter layer, and the exposed sample layer mounted on the filter. The holder's opening is larger at its lower surface than at its upper surface such, that the insert which is shaped as a four side truncated pyramid, can be placed into the holder from its lower surface but not through its upper surface opening. The layer filter with its mounted sample layer is sandwiched between the insert and holder to allow the sample to be exposed to incident X-rays through the holder's upper surface. Plastic tape or some other securing mechanism is used to secure the holder to the insert at the holder's lower surface. The result is a mount that allows easy installation and removal with automatic sample changers for X-ray diffraction of the membranes with no vertical offset and a flat, even, sample upper surface.

8 Claims, 5 Drawing Figures

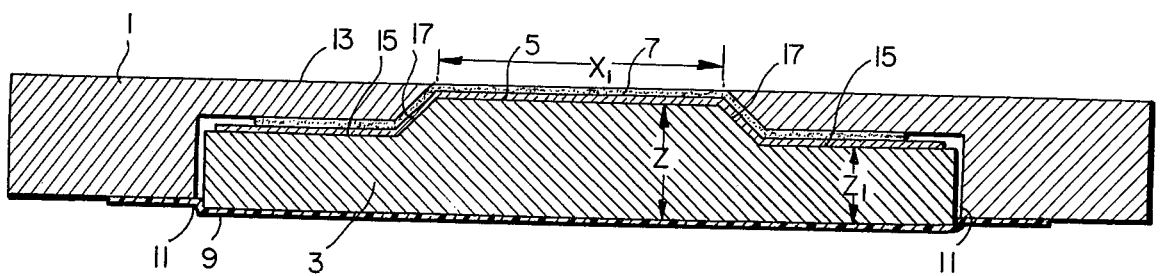
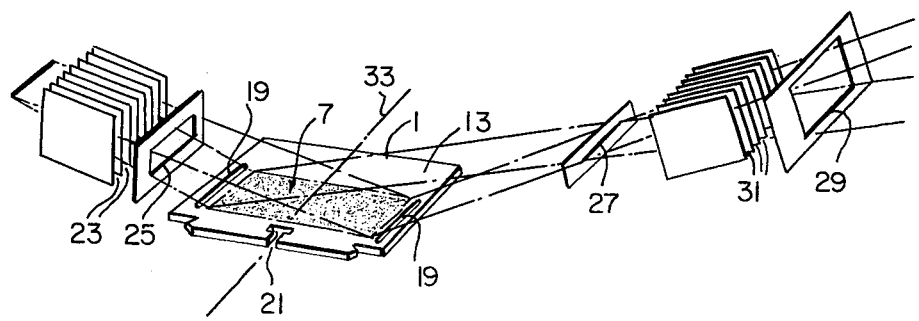

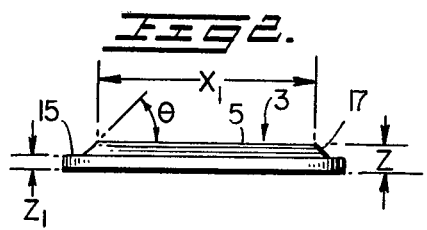
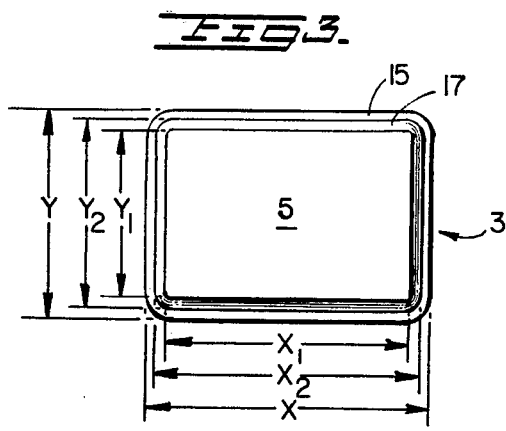
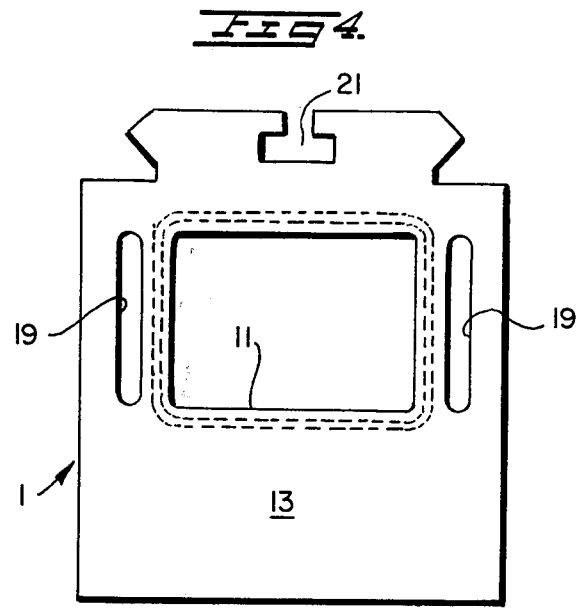

SAMPLE MOUNT FOR X-RAY DIFFRACTION

BACKGROUND OF THE INVENTION

1. Field of the Invention

Our invention is a mount specifically designed for use with an X-ray diffractometer.

2. Description of the Prior Art

Over the years various types of mounts have been used to mount specimens which are then subjected to some type of analysis. In one case the specimen is inserted in indents and held in place by a pair of brackets so that it may thereafter be exposed to a source of X-rays (U.S. Pat. No. 3,340,397 to R. L. Johnston). When X-ray diffraction is used as the technique to analyze the sample, a vacuum chuck can be used to hold the sample (U.S. Pat. No. 4,078,175 to J. C. Fletcher et al.) or it may be held or mounted in a rotatable holder (U.S. Pat. No. 3,852,594 to F. R. Paolini). Another mounting procedure useful with X-ray fluorescence, (U.S. Pat. No. 3,536,912 to W. Speck et al) provides for a suspended mount with adjusting screws to avoid static uncertainties.

U.S. Pat. No. 4,115,689 to V. Y. Won appears, at first glance, structurally close to this patent invention. However, the Won patent is designed specifically for X-ray fluorescence whereas our invention is concerned with X-ray diffraction. These two different uses bear on and specifically relate to the structural differences between the two inventions which make interchangeability virtually impossible. Although both X-ray fluorescence and X-ray diffraction employ the principles of Bragg's Law ($n\lambda = 2\theta \sin \theta$), in X-ray fluorescence the wavelength $\lambda$ is in the unknown and in X-ray diffraction the interplanar spacings (d) of the minerals are the unknowns. Our invention employs an especially selected filter which underlies the sample and in no way interfers with the diffracted incident X-ray beam whereas in the Won reference a plastic film is placed over the sample to keep the sample surface flat. If such a plastic film were used with X-ray diffraction the plastic itself would superimpose its own diffraction effects over those of the sample. With X-ray fluorescence, the method Won is specifically designed for, the plastic filter would have no effect. Other structural differences limiting our mounting to automatic sample changes useful for X-ray diffraction and Won's to X-ray fluorescence will become apparent as the remainder of this disclosure is read.

In the article authored by us entitled "A Metal-Membrane Mount for X-ray Powder Diffraction" first published on Apr. 1, 1979, in Volume 27, No. 2, pages 152–153 of the periodical "Clays and Clay Minerals" many of the details relating to this invention are disclosed including its mounting procedure. The contents of that article are specifically incorporated by reference herein.

SUMMARY OF THE INVENTION

This invention is a membrane mount specifically designed for use with an X-ray diffractometer. It was made to assure a flat even sample surface for the incident X-ray beam. Essentially the mount is made up of a mounting holder, a filter, and an insert which fits into the holder from its lower surface by way of a large opening therein. This same opening extends through the holder from its lower surface to its upper surface where it takes up less area. The insert is complementarily shaped to fit the holder at its side surfaces.

Pressed between the insert and holder is a layer filter substrate and thereupon the sample layer which is positioned to expose the sample at the holder's upper surface to incident X-rays. The filter is made of a material having a high mass absorption coefficient to prevent low angle scattering effects from incident rays. A holding device is used to keep the insert within the holder.

The principle object of this invention is an improved sample holder for use with an X-ray diffractometer.

More specifically it is holder designed for a sample that is classified as an oriented aggregate powder diffraction sample.

FIG. 1 is a cross-sectional view of the preferred embodiment of the invention with the insert held in its holder.

FIG. 2 is a side view of the insert.

FIG. 3 is an elevated view of the insert.

FIG. 4 is an elevated view of the holder.

FIG. 5 schematically illustrates how the sample holder fits into the geometry of an X-rayy diffractometer.

The essential components of the preferred embodiment of this invention are depicted in the FIG. 1 cross-section side view. These include the holder 1, the mount insert 3, the filter 5, and the sample layer 7 on the filter. In one embodiment a strip of plastic tape 9 is used as a fastner along the bottom of the insert and the holder to span the cavity therebetween and keep these members together. The preferred embodiment has the holder and insert made of metal, the filter of silver, and the tape of plastic. The insert fits into the lower or back side of the holder through a large opening 11 in the holder. The cut out interior surfaces of the holder's opening which are adjacent to the insert, when in place are shown, are complementarily shaped with the adjacent surfaces of the insert. The opening 11 extends completely through the holder and, due to its shape, is larger in area at the holder's lower surface than at the holder's surface 13. To be noted is the very level plane formed by the holder's upper surface with the sample layer 7 as it rests on the silver filter. Ideally this sample layer should be flush or at exactly the same plane as the upper surface 13. In order to insure that this critical feature is approached, as will be explained more fully hereafter, the dimensions and the orientation of the insert's surfaces 15 and 17—and hence their surfaces complements on the holder—firmly hold and position (along with the tape) the sandwiched filter and sample to provide for the smooth, planar, exposed upper surface of the sample so vitally essential to X-ray diffraction readings as practiced herein. In order to completely take up the area occupied by the opening of the holder at its upper surface and to provide overlapping edges, the surface area for both the filter substrate and the sample layer are each made substantially larger than the upper opening's area.

A better understanding of FIG. 1 may be had by referring to the two views of the insert shown in FIGS. 2-3. The holder shown in FIG. 4 into which this insert fits is basically a thin rectangular block with a rectangular opening (11) extending through the smallest or height dimension of the block. To properly fit into this unique shaped opening the insert is complementarily shaped in what as been termed a truncated four sided pyramid with a height Z. This is shown in FIGS. 2-3. For explanatory purposes the single piece insert may be thought of as being made up of a lower and a top portion. The lower portion of the insert comprises a rectangular shaped block whose upper surface is defined by horizontal surface 15, its height $Z_1$, and its length Y and width X. Integral with this lower base portion of the insert is a top smaller portion whose height is $Z-Z_1$, whose sides are the four angled surfaces 17, and whose top flat surface is the rectangle defined by the width $X_1$ and length by the dimension $Y_1$ (See FIG. 3). The larger rectangular base portion of the top portion of the insert is defined by the dimensions $X_2$ and $Y_2$ and joins the upper surface via the four surfaces 17 oriented at an angle $\phi$ (FIG. 2) from the flat surface 7. This angle $\phi$ is normally in the 30° to 45° range from the three parallel surfaces formed by the top of the insert, the filter and the sample with the angle 45° surface being used for the preferred embodiment. The insert's upper surface of the top portion is rectangular to fit the opening of the holder and defined by the dimensions of $X_1$ for its width and $Y_1$ for its length. In one working embodiment the mentioned dimensions had the following values in millimeters: $X_1=19.8$, $X_2=21.6$, $X=22.9$, $Y_1=14.7$, $Y_2=16.0$, $Y=17.8$, $Z_1=1,3$, $Z=1.9$, and $\phi=45°$. The holder for this same embodiment had a height of 1.9 (mm) outside dimensions of 42.0 (mm) and 23.1 (mm), and an upper surface opening of 15.0 mm by 20.0 mm. The four corners of the holder's upper surface opening were each rounded with a radius of 1.6 mm to facilitate machining and therefore make it less expensive. The silver filter used had a maximum thickness of 0.1 mm.

Silver filter 5 was specifically choosen as a substrate for the sample because it does not contribute to the detected diffracted X-ray beam at diffraction angles less than about 38° using copper radiation and it is not affected by the usual sample treatments. Filters made from materials that scatter the incident X-ray beam, such as glass or ceramics, would be totally unacceptable. Another possible more expensive material that would be acceptable for the filter is platinum since it, like silver, has a high mass absorption coefficient for the incident X-rays. As illustrated, the filter is a thin sheet which totally underlies the sample layer and may even extend beyond the surface area of the sample. One silver filter used had a series of 0.45 micron sized holes.

The function of the plastic tape backing 9 is to hold the insert in the opening of the membrane holder. When so used the edges of the filter and sample layer are pressed between the insert and holder and held in place. As will be discussed with respect to FIG. 5 other types of holding devices, like clips, can be used to keep the insert, filter and sample layer in the holder. Some depend on the particular feed mechanism of the diffractometer which may vary with the manufacturer selected.

FIG. 5 illustrates the use of this invention with a diffractometer. The holder (as in FIG. 4) has been modified from that shown in FIG. 1 and is a Philip's sample mount manufactured by (Philip's Electronic Instruments, Inc., of Mahwah, New Jersey. As in FIG. 4, except for the addition of two slots 19 on either side of the main opening and the key hole by arrangement 21, the holder is the same as that of FIG. 1. These two variations serve to feed the holder and keep it properly aligned as a divergent beam of X-rays from the narrow line source X passes through the divergence slit 25 to large flat sample layer 7. The diffracted X-ray beam converges at the receiving slit 27 and continues to the counter tube (not shown) which is placed beyond the antiscatter slit 29. The parallel slits 31 limit the X-ray beams divergence in a plane normal to the axis of rotation 33 of the specimen. The distance from sorce X to the axis of rotation 33 must be equal to the distance from the same axis to the receiving slit 27. A drive mechanism of a goniometer moves the detector at a constant speed that is twice the constant angular speed of the specimen. This means the flat surface of the specimen is always at angle $\theta$ when the detector is at an angle $2\theta$. The pattern detected is recorded using a count-rate meter attached to a strip chart recorder. The resulting charge would show intensities or peaks as a function of reflected angles $2\theta$. Using Bragg's law and the fact that no two chemically distinct substances give identical patterns, identification becomes possible.

It should be clear that certain features of this invention are critical to its operation. One of the most important is the overlap of the filter and sample layer as they are pressed between the insert and holder. The angle $\phi$ (FIG. 2) is preferably about 30° to 45°, however, it should not be much steeper as this may sheer the filter and sample layer. If the angle was less than 30° the insert may not easily hold the filter and sample firmly to be sure their upper surfaces are as flat and smooth as required. This flatness assures good results and workability in the sample changer. Unless the sample layer and its filter are held very flat and smooth the detected diffracted beam will not give an accurate result since the diffraction geometry will be off. Unless the material chosen for the new filter is made from a material with a high mass absorption coefficient, the substrate will create its own background of scattered radiation which, of course, could mask the sample's pattern and therefore complicate interpretation.

The primary use of this invention is for X-ray powder diffraction with oriented aggregate samples. Tests we have conducted were done on clay samples prepared in this manner. Other materials, organic or inorganic, could also be prepared as samples for use with this material, especially where preferred orientation is desirable.

A good source of information which discusses this oriented aggregate method of preparing samples in a water suspension is the incorporate article "A Metal-Membrane Mount for X-ray Powder Diffraction" first published on Apr. 1, 1979, in Volume 27, No. 2, pages 152-153 of the periodical "Clays and Clay Minerals". Other types of methods used to prepare random powder samples, or single crystal diffraction samples, are not applicable for use with this invention since these samples are not mounted on filter substrates.

To those skilled in the art of X-ray diffraction techniques, other variations may also be possible. None should be used to limit the scope and extent of our invention which is to be measured only by the claims which follow.

We claim:

1. A sample mounting assembly for use with an X-ray diffractometer comprising:
    a membrane holder with an upper and a lower surface opposite each other, said holder having an opening extending therethrough from the lower to the upper surface with the area of the opening at the lower surface being larger than the area of the opening at the upper surface;
    an insert having an upper and lower surface and adapted to fit into the holder's opening from the holder's lower surface and complementary shaped at its side surfaces with the mating edge surfaces of the holder to prevent the insert, when properly fitted therein, from moving through the holder;

a filter substrate layer larger than the area of the holder's upper opening and adapted to fit between the insert and holder in that opening, said filter being made of a material having a high mass absorption coefficient for X-rays;

a sample layer of material, which is to be subjected to X-ray diffraction analysis, mounted on said filter layer to form an exposed flat layer at the upper opening even with the adjacent upper surface of the holder, said sample overlapping the filter and being pressed at its edge between the insert and holder;

and means for holding the insert in the holder.

2. The assembly of claim 1 wherein:
said insert's surfaces are parallel at its upper and lower surfaces, and the insert is shaped as a truncated four sided pyramid at its upper edge surfaces.

3. The assembly of claim 1 wherein:
said insert's side surfaces form, at least along a portion therewith, an angle of at least 30 degrees but no more than 45 degrees with the insert's upper surface.

4. The assembly of claim 2 wherein:
the insert's truncated side surfaces are angled at least 30 degrees but no more than about 45 degrees from the insert's upper surface.

5. The assembly of claim 1 wherein:
the filter layer is made from silver and the sample layer is prepared by utilizing a water sample in suspension to form by filtration the layer on the filter.

6. The assembly of claim 1 wherein the holder's opening at the lower surface is at least ten percent larger in area than at the upper surface to provide for an overlapping portion of the holder over the insert with the filter and sample layer therebetween.

7. The assembly of claim 6 wherein the filter layer is made from silver and the sample layer a clay material made from water suspension to provide a oriented aggregate powder suitable for X-ray diffraction analysis.

8. The assembly of claim 1 wherein the filter layer, the sample layer, and the upper surface of the insert are all parallel to each other along their major surface areas.

* * * * *